(12) United States Patent
Molloy et al.

(10) Patent No.: US 11,969,441 B2
(45) Date of Patent: *Apr. 30, 2024

(54) PREVENTION OF INFECTION BY HIGHLY PATHOGENIC VIRUSES USING TOPICAL APPLICATION OF POVIDONE-IODINE ON MUCOUS MEMBRANES

(71) Applicant: FIREBRICK PHARMA LIMITED, Melbourne (AU)

(72) Inventors: Peter Molloy, Doreen (AU); Stephen Goodall, Doreen (AU)

(73) Assignee: FIREBRICK PHARMA LIMITED, Melbourne (AU)

( * ) Notice: Subject to any disclaimer, the term of this patent is extended or adjusted under 35 U.S.C. 154(b) by 133 days.

This patent is subject to a terminal disclaimer.

(21) Appl. No.: 17/544,926

(22) Filed: Dec. 7, 2021

(65) Prior Publication Data

US 2022/0168338 A1    Jun. 2, 2022

Related U.S. Application Data

(63) Continuation of application No. 16/925,740, filed on Jul. 10, 2020, now Pat. No. 11,246,887, which is a continuation of application No. PCT/AU2020/050586, filed on Jun. 10, 2020.

(30) Foreign Application Priority Data

Jun. 10, 2019 (AU) ................................ 2019902006
Feb. 20, 2020 (AU) ................................ 2020900489

(51) Int. Cl.
| | | |
|---|---|---|
| A61K 31/79 | (2006.01) | |
| A61K 9/00 | (2006.01) | |
| A61K 9/08 | (2006.01) | |
| A61K 9/127 | (2006.01) | |
| A61K 33/18 | (2006.01) | |
| A61K 47/32 | (2006.01) | |
| A61P 31/04 | (2006.01) | |
| A61P 31/12 | (2006.01) | |
| A61P 31/14 | (2006.01) | |
| A61P 31/16 | (2006.01) | |

(52) U.S. Cl.
CPC ............ *A61K 33/18* (2013.01); *A61K 9/0043* (2013.01); *A61K 9/08* (2013.01); *A61K 9/127* (2013.01); *A61K 47/32* (2013.01)

(58) Field of Classification Search
None
See application file for complete search history.

(56) References Cited

U.S. PATENT DOCUMENTS

| | | | |
|---|---|---|---|
| 4,523,589 A | 6/1985 | Krauser | |
| 11,246,887 B2 * | 2/2022 | Molloy | ................... A61K 9/08 |
| 2003/0180380 A1 * | 9/2003 | Hansen | ................ A61K 9/0043 |
| | | | 424/661 |
| 2006/0122082 A1 | 6/2006 | Paul | |
| 2006/0148726 A1 * | 7/2006 | Berg | ....................... A61P 31/12 |
| | | | 514/456 |
| 2008/0138438 A1 | 6/2008 | Taylor et al. | |
| 2017/0165296 A1 * | 6/2017 | Goodall | .................. A61P 31/00 |

FOREIGN PATENT DOCUMENTS

| | | |
|---|---|---|
| CN | 1203864 C | 6/2005 |
| CN | 103751274 A | 4/2014 |
| EP | 0526695 B1 | 2/1998 |
| JP | H04173726 A | 6/1992 |
| JP | H09151127 A | 6/1997 |
| JP | 2000169378 A | 6/2000 |
| JP | 2004352642 A | 12/2004 |
| KR | 1020170033925 A | 3/2017 |
| KR | 101935250 B1 | 1/2019 |
| WO | 2012177251 A1 | 12/2012 |
| WO | 2016011496 A1 | 1/2016 |
| WO | 2020232515 A1 | 11/2020 |

OTHER PUBLICATIONS

Pelletier et al., "Efficacy of Povidone-Iodine Nasal and Oral Antiseptic Preparations against Severe Acute Respiratory Syndrome-Coronavirus 2 (SARS-COV-2)" MedRxiv, May 2020, pp. 1-7. (Year: 2020).*
Mäkelä, Mika J. et al., "Viruses and bacteria in the etiology of the common cold", Journal of clinical microbiology 36.2, 1998, pp. 539-542.
Wutzler P, et al., "Virucidal Activity and cytotoxicity of the liposomal formulation of Povidone-iodine" Antiviral Research, Elsevier BV, NL, vol. 54, Jan. 1, 2002, pp. 89-97.
Kramer A. et al, "New Aspects of the Tolerance of the Antiseptic Povidone-Iodine in Different ex vivo Models," Dermatology, 2002, vol. 204. Supplement 1, p. 86-91.
Reimer, K. et al, "Antimicrobial Effectiveness of Povidone-Iodine and Consequences for New Application Areas", Dermatology, 2002, vol. 204, Supplement 1, pp. 114-120.
Rombaux, P., et al., "The role of nasal cavity disinfection in the bacteriology of chronic sinusitis", Rhinology, Jun. 2005, vol. 43, No. 2, pp. 125-129.
Chepla K. et al, "Interstitial Pneumonitis After Betadine Aspiration," The Journal of Craniofacial Surgery, 2012, vol. 23(6), p. 1787-1789.
Unknown, "Betadine Ready to use Sore Throat Gargle®," Consumer Medicine Information Leaflet, Retrieved from internet on Jul. 29, 2021, URL:https://medsafe.govt.nz/consumers/cmi/b/betadine. pdf, Published on Nov. 4, 2019, pp. 1-3.
Joseph, A. et al, "The Basics: What We Know—and Don't Know—About the Virus Spreading in China and Beyond," STAT, Jan. 22, 2020, pp. 1-8.

(Continued)

*Primary Examiner* — Brian Gulledge
(74) *Attorney, Agent, or Firm* — Rimon PC (57) ABSTRACT

This invention is directed to methods for prevention of infections by highly pathogenic viruses by applying to the nasal mucous membranes topical preparations comprising the broad-spectrum antimicrobial agent povidone-iodine.

4 Claims, 2 Drawing Sheets

(56) References Cited

OTHER PUBLICATIONS

Pelletier et al, "Efficacy of Povidone-Iodine Nasal And Oral Antiseptic Preparations Against Severe Acute Respiratory Syndrome-Coronavirus 2 (SARS-COV-2)," medRxiv, May 26, 2020, pp. 1-7.

* cited by examiner

PREVENTION OF INFECTION BY HIGHLY PATHOGENIC VIRUSES USING TOPICAL APPLICATION OF POVIDONE-IODINE ON MUCOUS MEMBRANES

CROSS-REFERENCE TO RELATED APPLICATIONS

The present application is a Continuation application of U.S. application Ser. No. 16/925,740, filed Jul. 10, 2020, which is a Continuation of International Patent Application No. PCT/AU2020/050586, filed Jun. 10, 2020, which claims priority to Australian patent application no. 2020900489, filed Feb. 20, 2020, and Australian patent application no. 2019902006, filed Jun. 10, 2019, the contents of each of which are incorporated herein by reference in their entirety.

FIELD OF THE INVENTION

This invention is directed to methods for prevention of infections by highly pathogenic viruses by applying to the nasal mucous membranes topical preparations comprising the broad-spectrum antimicrobial agent povidone-iodine.

BACKGROUND OF THE INVENTION

Diseases caused by, generally zoonotic, highly pathogenic viruses are of increasing concern to health authorities. Prominent recent examples are the outbreaks of diseases caused by the SARS and MERS coronaviruses (SARS-CoV, MERS-CoV), the avian influenza virus (AIV), Ebola virus (EBOV) and the virus responsible for COVID19 (SARS-CoV-2). With increasing globalization, the threat of diseases caused by such highly pathogenic viruses has been amplified. In some cases, there is the added concern that the viruses could be used for bioterrorism.

For the purposes of this invention, the term highly pathogenic viruses or HP viruses will be used, where the term includes all viruses where there is limited access to effective treatment or vaccines, because there are currently no effective treatment or vaccines or where they exist but deployment of such interventions is compromised or contraindicated (for example, the use of treatments that may be unsuitable for patients with other concomitant morbidities or there may be delays in vaccine deployment) and where the viruses are capable of causing serious disease, including fatal disease, in humans if untreated and/or significant societal impact, including the potential to be used as bioterror weapons.

By way of specific example, HP viruses will include the following: Filoviridae able to cause fatal viral haemorrhagic fever (VHF) in humans, notably EBOV, Marburg virus (MARV), Sudan virus (SUDV), Tai Forest virus (TAFV) and Bundibugyo virus (BDBV); coronaviruses able to cause serious or fatal illness in humans notably MERS-CoV, SARS-CoV and SARS-CoV-2; and avian influenza virus (AIV) and other emergent strains of influenza with pandemic potential. It will be understood that other emergent viruses of similar potential impact and concern may be identified in the future, either as a result of a marked change in the transmission potential of a known virus or emergence of a new species or strain.

Apart from the fact that all these viruses are capable of causing serious and fatal illness in humans and that an effective treatment or vaccine may not yet exist, or be contraindicated and/or difficult to rapidly deploy, the other important commonality is that they are all zoonotic, i.e. originally transmitted from animals to humans. By way of example, the animal source for AIV is birds, and for EBOV it is believed to be fruit bats.

Another common feature is that they have relatively high mortality rates in humans and in many cases are readily transmissible, often via the respiratory route. Typically these viruses will be categorised as level 3 or 4 risk groups and in many cases defined as biological select agents by regulatory authorities such as in the USA. In some cases, such as novel, emergent influenza viruses and SARS-CoV-2, they have the potential to become pandemic, causing significant societal impact, large numbers of deaths and major challenges for frontline healthcare workers who are at risk of contracting the virus. A further concern is that some of the viruses responsible for these diseases may have the capacity to be developed as bioterror weapons.

Ebola

Ebola viruses are of particular concern. They cause a VHF that is known as Ebola virus disease (EVD) or simply Ebola, which in 2014 killed more than 9,000 people in West Africa and caused global concern. For the purposes of this invention, the term "Ebolavirus" will be deemed to include all five filoviruses viruses capable of causing human VHF, namely EBOV, MARV, SUDV, TAFV and BDBV.

Fruit bats are believed to be the natural reservoir of EBOV and contact with bat faeces or other body fluids may be responsible for the initial infection of humans, after which human-human transmission can occur. As noted by Osterholm et al ("Transmission of Ebola Viruses: What We Know and What We Do Not Know." mBio, 6, 2 (2015): 1-9) human-to-human transmission of EBOV occurs principally via direct contact with blood or bodily fluids from an infected person who is showing signs of infection or by contact with objects recently contaminated by an actively ill infected person.

Bosio et al ("Ebola and Marburg Viruses Replicate in Monocyte-Derived Dendritic Cells without Inducing the Production of Cytokines and Full Maturation." The Journal of Infectious Diseases 2003; 188:1630-8) reported that the profound virulence of EBOV and MARV is due to their ability to infect and replicate in dendritic cells and monocytes undetected until the numbers of virus are beyond the ability of the host immune response to contain the infection. The infected immune cells then propagate the infection through the body.

Mohomadzadeh et al ("How Ebola and Marburg viruses battle the immune system." Nature Reviews Immunology 7, (2007): 556-567) also reported that productive infection, that is infection that results in more viral progeny being produced, occurs primarily in dendritic cells, monocytes and macrophages.

Osterholm et al (2015) hypothesized that Ebolaviruses have the potential to be respiratory pathogens with primary respiratory spread by aerosolization of droplet micronuclei following coughing and vomiting by Ebola sufferers. EBOV has been found on the outside of face masks worn by health workers caring for victims of the disease and it has been established that the virus can infect certain cells of the respiratory tract.

Prescott et al ("Postmortem Stability of Ebola Virus." Emerging Infectious Diseases, Vol. 21, No. 5, May 2015: 856-859), reported that based on animal models the virus can be isolated from corpses for at least seven days after death, with large numbers of virus found in the nasal and oral cavities.

Osterholm et al (2015) also reported that the infectious dose for Ebolaviruses in humans appears to be extremely low, with ten or fewer viral particles being sufficient for infection placing healthcare workers at risk despite barrier prevention procedures.

Because of these factors, and other factors, such as environmental conditions and training, standard barrier protection procedures, such as hand hygiene and personal protective equipment (PPE) such as gloves, masks, eye protection and respirators, may not be sufficient to prevent infection of healthcare workers from Ebola. This is evidenced by the World Health Organization's review of healthcare worker infections during the 2013-16 Ebola epidemic and publication of the draft discussion paper "Preferred Product Characteristics for Personal Protective Equipment for the Healthcare Worker on the Frontline Responding to Ebola Virus and Haemorrhagic Fever Outbreaks in Tropical Climate (WHO 7 Sep. 2017). Meanwhile, those exposed without PPE, such as family members, are at high risk of infection. Therefore, the need exists to better protect healthcare works and civilians who might be exposed to Ebolaviruses, when exposed to infected people and their body fluids.

Pandemic Influenza

Like Ebola, pandemic influenza is a potentially fatal illness that continues to cause global concern. It is caused by of the introduction of an influenza virus with high pathogenic potential into a naïve human population that has no pre-existing immunity and often whose natural host is an animal—for example, birds in the case of avian influenza virus (AIV) and pigs in the case of swine influenza—or a recombinant virus containing human virus derived genes together with genes not previously found in human isolates. One of the most highly pathogenic strain of AIV to date is denoted H5N1 and has been spreading throughout Asia since 2003. Other known and potentially highly pathogenic strains are H5N9, H7N3, H7N7, H7N9, and H9N2. The most recent 2009 pandemic "swine flu" virus (generally believed to be a reassortment of bird, swine, and human flu viruses) is designated H1N1, specifically (H1N1)pdm09 and is reported to have been associated with 151,700-575,400 deaths worldwide in the first year of the pandemic. It is generally believed that most initial human infections of AIV are a result of either handling dead infected birds or from direct contact with infected fluids. However, once a person is infected, the risk of human-human transmission is of notable concern possibly by analogy with other human influenza viruses through aerosolization of the virus during coughing and sneezing and subsequent inhalation by others. Human-human transmission can also occur through contact of mucous membranes (for example of the eyes or nasal passages) with body fluids and touching objects contaminated with the virus.

Outbreaks of AIV and other emergent influenza viruses are managed by practices such as the elimination of the infected animals, isolation of infected people, screening at airports for people with influenza symptoms, wearing of facemasks by civilians who perceive they might be at risk, and adherence to strict barrier protection and infection control procedures by healthcare workers, including hand hygiene and personal protective equipment (PPE) such as gowns, gloves, eye protection and respirators.

Existing antiviral agents such as zanamivir and oseltamivir have been of limited effectiveness in treating AIV infections, because by the time the patient presents it is generally too late in the infection. Further, the virus has demonstrated the ability to mutate and thereby circumvent such drugs, particularly oseltamivir, in some cases. Efforts are also underway to develop vaccines but no effective vaccine for all pandemic strains has become available to date and, despite many attempts, no universal vaccine has been developed.

Given these considerations and the fact that the virus is spread through airborne transmission, there is the grave concern that AIV and related influenza viruses could be used as a bioterror weapon.

The need exists to better protect healthcare workers and civilians who might be exposed to emergent influenza viruses of high pathogenicity, either when handling infected animals or when exposed to infected people.

SARS and MERS

Like AIV, Severe Acute Respiratory Syndrome or SARS is a potentially fatal illness caused primarily by airborne transmission of a virus and primary infection of the respiratory tract. SARS is caused by a coronavirus, called SARS-associated coronavirus or SARS-CoV. Coronaviruses are a family of single-stranded enveloped RNA viruses that are divided into four major genera. The genome sequence of SARS-CoV-2 is 82% similar to severe acute respiratory syndrome coronavirus (SARS-CoV), and both belong to the β-genus of the coronavirus family. Human coronaviruses such as SARS-CoV and Middle East respiratory syndrome coronavirus (MERS-CoV), are known to cause respiratory and enteric symptoms. SARS was first reported in Asia in February 2003. The illness spread to more than two dozen countries before the global outbreak of 2003 was finally contained. During 2003, a total of 8,098 people worldwide were infected with SARS and 774 died. In late 2019 the world witnessed the emergence of the novel coronavirus (SAR-CoV-2) which caused a new acute respiratory syndrome designated COVID-19 and which was later designated as a global pandemic.

Early symptoms include a high fever, headache, malaise and body aches. Some also have mild respiratory symptoms or diarrhoea. After 2 to 7 days, SARS patients may develop a dry cough. Many patients develop pneumonia, which is the principal cause of mortality.

SARS-CoV is transmitted by respiratory droplets produced when an infected person coughs or sneezes, with the infected droplets deposited on the mucous membranes of the mouth, nose, or eyes of people who are nearby. The virus also can spread when a person touches a surface or object contaminated with infectious droplets and then touches his or her mouth, nose, or eyes.

MERS is also a serious and often fatal respiratory illness in humans caused by a novel coronavirus, designated MERS-CoV. MERS was first found in the Arabian Peninsula and believed to originate in camels. Between September 2012 and Jun. 5 2015, there had been 1279 human cases of MERS reported and 495 deaths, or a mortality rate of 38.7%. The disease was first reported in Saudi Arabia but more recently was found in Korea and more than 20 other countries.

MERS-CoV, like other coronaviruses, is thought to spread from an infected person's respiratory secretions, such as through coughing. Early symptoms may include fever, chills, coughing, shortness of breath, body aches, sore throat, headache, diarrhoea, nausea and/or vomiting, and runny nose. However, a wide clinical spectrum of MERS-CoV infection has been reported, ranging from asymptomatic infection to acute upper respiratory illness, and rapidly progressive pneumonitis, respiratory failure, septic shock and multi-organ failure resulting in death.

Those at primary risk of infection include frontline healthcare workers and the families of those infected. Those at secondary risk include airline flight crews, Emergency Medical Service (EMS) units at airports, customs and immigration personnel and international travelers. For healthcare workers, recommended protection includes hand hygiene, gloves, gowns, eye protection and respirators.

For both SARS and MERS, recommended protection for frontline healthcare workers includes hand hygiene and personal protective equipment (PPE) such as gowns, gloves, eye protection and respirators. However, such protections may not be fully effective and may not be available to all healthcare workers and others who may be exposed.

Protection from Highly Pathogenic (HP) Viruses

Unbroken epidermal skin provides an effective barrier against the invasion of microbes into the human body, including invasion by HP viruses. However, mucous membranes, such as in the eyes, nasal passages, oral cavity and lungs are more permissive and so provide a more receptive surface for microbial ingress and systemic infection. The nasal passages also provide an effective entrapment mechanism to prevent particles and aerosols, including microbes, from being transported further along the airways to the bronchioles and lungs. This filtration mechanism arguably results in accumulation of viruses and bacteria in the nasal passages where they are able to proliferate, requiring the body to mount an immune defence to counter the burgeoning viral load. The escalating viral load within the nasal passages increases the risk of the virus finding its way into the lungs, such as in MERS and SARS, or spreading systemically through the body.

SUMMARY OF THE INVENTION

The present invention involves methods for reducing the risk of transmission or preventing infection by HP viruses by application of PVP-I preparations to the nasal passages of subjects who have been exposed to or may be exposed to HP viruses, this would also include reducing the risk of infection or transmission of infection from people suspected of shedding HP viruses (for example, people believed to be infected or at risk of being infected as a consequence of prior exposure to a potential source of infection).

In all cases, the methods involve the application of pharmaceutical preparations to the nasal passages of human subjects, said preparations comprising at least 0.10% w/v and no more than 1.25% w/v PVP-I. In all cases, the application may occur before, after or around the time of exposure of the subject to a person or people infected (or maybe infected) with HP viruses or other sources of infection. In all cases, the applications occur at a frequency of between 1 and 12 times daily and continue at a suitable daily frequency for a number of days after any such exposure depending on the incubation period for infection caused by each virus.

Accordingly in one aspect, the present invention provides a method for reducing the risk of infection or transmission of infection by EBOV capable of causing Ebola virus disease, by application of a PVP-I preparation comprising between 0.10% w/v and 1.25% w/v PVP-I to the nasal passages of a subject exposed or potentially exposed to EBOV, said application occurring with a frequency of between 1 and 12 times daily commencing before, after or around the time of exposure to the virus and/or thereafter for preferably up to 21 days.

In another aspect the present invention provides a method for reducing the risk of infection or transmission of infection by filoviruses other than EBOV, including MARV, SUDV, TAFV and BDBV, capable of causing viral haemorrhagic fevers, by application of a PVP-I preparation comprising between 0.10% w/v and 1.25% w/v PVP-I to the nasal passages of a subject exposed or potentially exposed to the filoviruses, said application occurring with a frequency of between 1 and 12 times daily commencing before, after or around the time of exposure to the virus and/or thereafter for preferably up to 21 days.

In another aspect the present invention provides a method for reducing the risk of infection or transmission of infection by the avian influenza viruses (AIV) designated H5N1 that is capable of causing pandemic influenza, by application of a PVP-I preparation comprising between 0.10% w/v and 1.25% w/v PVP-I to the nasal passages of a subject exposed or potentially exposed to H5N1, said application occurring with a frequency of between 1 and 12 times daily commencing before, after or around the time of exposure to the virus and/or thereafter for preferably up to 8 days.

In another aspect the present invention provides a method for reducing the risk of infection or transmission of infection by pandemic influenza viruses other than H5N1 including H5N9, H7N3, H7N7, H7N9, H9N2 and H1N1 that are capable of causing serious or pandemic influenza, by application of a PVP-I preparation comprising between 0.10% w/v and 1.25% w/v PVP-I to the nasal passages of a subject exposed or potentially exposed to the viruses, said application occurring with a frequency of between 1 and 12 times daily commencing before, after or around the time of exposure to the virus and/or thereafter for up to preferably 21 days, such as up to 8 days.

In another aspect the present invention provides a method for reducing the risk of infection or transmission of infection by SARS-CoV capable of causing Severe Acute Respiratory Syndrome (SARS), by application of a PVP-I preparation comprising between 0.10% w/v and 1.25% w/v PVP-I to the nasal passages of a subject exposed or potentially exposed to SARS-CoV, said application occurring with a frequency of between 1 and 12 times daily commencing before, after or around the time of exposure to the virus and/or thereafter for up to preferably 21 days, such as up to 10 days.

Accordingly in one aspect, the present invention provides a method for reducing the risk of infection or transmission of infection by SARS-CoV-2 capable of causing COVID-19 disease by application of a PVP-I preparation comprising between 0.10% w/v and 1.25% w/v PVP-I to the nasal passages of a subject exposed or potentially exposed to SARS-CoV-2, said application occurring with a frequency of between 1 and 12 times daily commencing before, after or around the time of exposure to the virus and/or thereafter for up to preferably 21 days.

In another aspect the present invention provides a method for reducing the risk of infection or transmission of infection by MERS-CoV capable of causing Middle East Respiratory Syndrome (MERS), by application of a PVP-I preparation comprising between 0.10% w/v and 1.25% w/v PVP-I to the nasal passages of a subject exposed or potentially exposed to MERS-CoV, said application occurring with a frequency of between 1 and 12 times daily commencing before, after or around the time of exposure to the virus and/or thereafter for up to preferably 21 days.

In another aspect the invention provides a method of decreasing the release of a HP virus from the respiratory tract, primarily from the nasal passages, of a person infected with the HP virus, the method comprising application to the nasal passages of the infected person an effective amount of a pharmaceutical preparation comprising povidone-iodine (PVP-I) at a concentration of greater than 0.10% w/v and less than about 1.25% w/v. For instance, the present inventors have shown marketed reduction of the replication of SARS-CoV-2 in the presence of the PVP-I formulation according to the present invention. In this regard the reduction of measurable viral growth after PVP-I exposure was observed to be at least −2.4 Log 10 which represents a reduction in viral RNA copies of over 99%.

Figure 1:
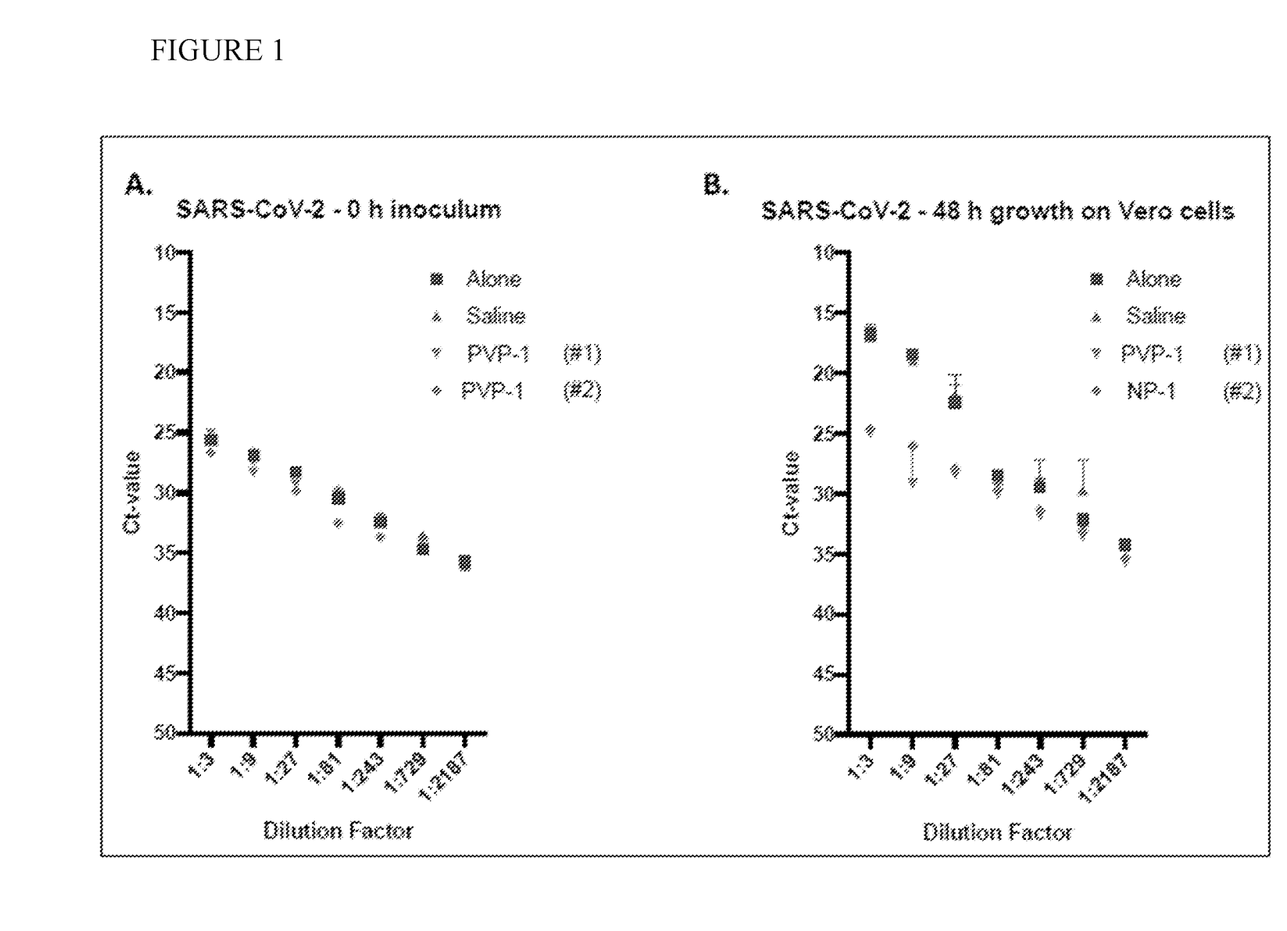
FIG. 1: Detection of SARS-CoV-2 RNA in 96-well plate supernatants by real-time TaqMan RT-PCR post exposure to test solutions. SARS-CoV-2 was exposed to the indicated test solution(s) for 1 minute before serial dilution (1:3) and incubation on Vero cells for 48 h. Values expressed as mean cycle threshold (Ct) value+SEM (n=3) versus dilution factor (1:3 increments) (A) Time point zero (0 h) inoculum titration used to determine baseline Ct-values of treated samples. (B) Culture supernatants harvested 48 h post-inoculation on to Vero cells.
Figure 2:
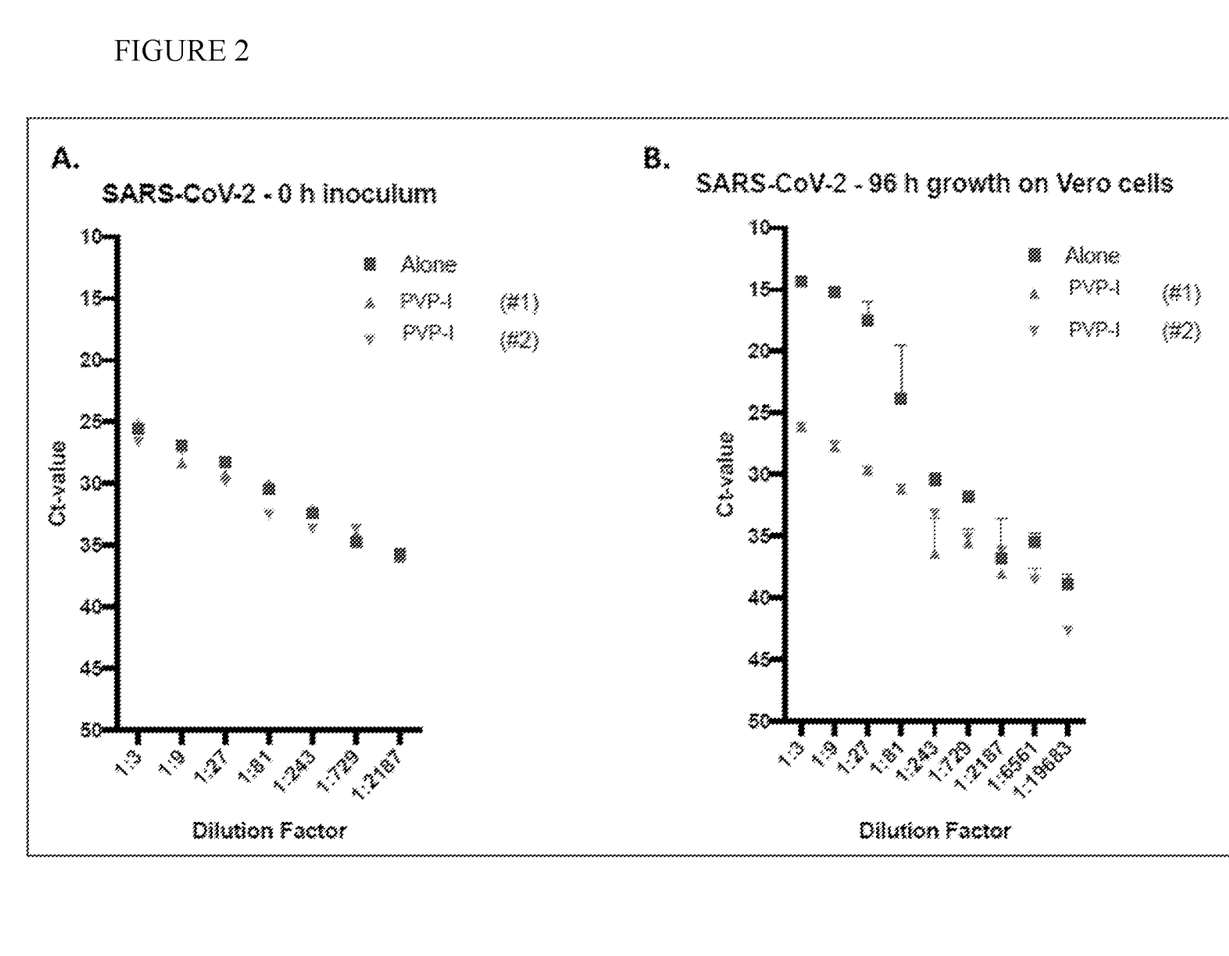
FIG. 2: Detection of SARS-CoV-2 RNA in 96-well plate supernatants by real-time TaqMan RT-PCR post exposure to test solutions. SARS-CoV-2 was exposed to the indicated test solution(s) for 1 minute before serial dilution (1:3) and incubation on Vero cells for 96 h. Values expressed as mean cycle threshold (Ct) value+SEM (n=3) versus dilution factor (1:3 increments) (A) Time point zero (0 h) inoculum titration used to determine baseline Ct-values of treated samples. (B) Culture supernatants harvested 96 h post-inoculation on to Vero cells.

It is evident from the Figures and experimental contained herein that SARS-CoV-2 replication was effectively eliminated in the samples exposed to PVP-I, as evidenced by the lack of detection of virus-specific RNA in samples grown on Vero cells compared to untreated control samples. These data correspond to a reduction of viable, replication competent SARS-CoV-2 by >99.97% compared to control values. Notably, and surprisingly, the virus associated RNA in the inoculum samples was not depleted by PVP-I treatment. These data highlight that a) PVP-I did not interfere with the RT-PCR assay method and therefore the RNA detection data are valid; b) it is essential that a method involving culture of the virus, as described in the present example, be used to detect the effect of PVP-I on virus viability. In the absence of a culture step to establish viral replication competence the effect of PVP-I may have been obscured.

It is taught herein that the application may occur with a frequency of between 1 and 12 times daily commencing before, after or around the time of exposure to the virus and/or thereafter for up to 21 days (or for the period of suspected shedding should symptoms persist and/or there is any other concern, for example a positive diagnostic test, that the subject may still be shedding).

In another aspect the invention provides a method of decreasing the impact of secondary infections of a person infected with a primary HP virus, the method comprising application to the nasal passages of the infected person an effective amount of a pharmaceutical preparation comprising povidone-iodine (PVP-I) at a concentration of greater than 0.10% w/v and less than about 1.25% w/v. Said application occurring with a frequency of between 1 and 12 times daily commencing after or around the time of exposure to the primary virus and/or thereafter for up to preferably 14 days (or for the period symptoms associated with the primary and/or secondary persist and/or there is any other concern, for example a positive diagnostic test, that the subject may still be infected).

DETAILED DESCRIPTION OF THE INVENTION

To date, PVP-I has never been proposed as a preventative for infections caused by HP viruses by application to the nasal passages. Its use as a topical antiseptic on hands and skin to prevent infection by viruses, including HP viruses, is known and widely applied as part of barrier regimens for preventing access of the virus to the interior of the human body.

Australian patent application 2014206143 to Molloy and Goodall, discloses that application of PVP-I to the nasal passages can be used to treat and prevent infections caused by common cold viruses, but there is no suggestion that a similar application to the nasal passages could prevent infection and/or shedding by/of HP viruses or diseases associated with secondary infections, nor is it obvious because SARS, MERS and AIV, for example, are considered lower respiratory tract infections (LRI) with very different clinical presentation and pathology to an infection limited to the upper respiratory tract (URI) such as the common cold. Furthermore Ebola is considered to be a consequence of systemic infection.

The present invention discloses for the first time that application of PVP-I to the nasal passages has utility in the reduction of risk of infection and transmission of infection, the prevention of illness as well as the decrease risk of secondary infections caused by and associated with HP viruses such as Ebolaviruses, such as EBOV, pathogenic coronaviruses, such as SARS-CoV and MERS-CoV, and pandemic influenza viruses, such as AIV, and other emergent HP viruses.

EBOV

In the case of EBOV and other filoviruses, whether the exposure occurs by direct contact with infected body fluids or through airborne virus, at some point the virus needs to gain access to the internal human body in order to initiate and propagate the infection. A likely portal for such access is the mucous membranes of the face, the respiratory tract and in particular the nasal passages.

As is the case with the common cold, the eyes may be one portal, as could occur when someone rubs their eyes with fingers contaminated with virus. However due to the physiology of the human body it is most likely that any virus entering through the eyes would find its way to the nasal passages and replicate there as part of the process of establishing a productive infection.

The oral cavity might also be a useful portal for the virus but the constant secretion of saliva and excretory mechanisms such as swallowing would argue against this as an important access point for the virus. In contrast, the nasal passages represent a highly receptive area for an infection and in the absence of a cold or other nasal infection, secretions are limited and as taught by Australian patent application 2014206143 to Molloy et al, previously referenced herein, normal mucociliary clearance takes around 15 minutes. The nasal passages offer another important advantage for filoviruses such as EBOV in that the nasal passages contain monocytes that act as sentinel cells for infection, also as taught in Australian Patent 2014206143 to Molloy et al, previously referenced herein. Such immune cells are known to become infected by EBOV and to act as a 'Trojan horse' for the EBOV infection that spreads to organs throughout the body. These immune cells are not commonly found in the oral cavity.

Further the presence of EBOV or EBOV RNA in the nasal passages would cause the monocytes to release cytokines thereby attracting neutrophils to the nasal passages, which would also be susceptible to infection by EBOV and in fact, rather than only fight the infection, which is their normal role, it is postulated that their infection would accelerate and propagate the infection along with the infected monocytes.

Therefore, the present invention discloses for the first time that through the unexpected combination of these factors, the nasal passages surprisingly offer a uniquely attractive portal for an initial entry of EBOV into the human host as a prelude to systemic replication and disease. However, it is this point of entry that also makes EBOV especially susceptible to attack and destruction by PVP-I through application to the nasal passages.

It is known that PVP-I rapidly destroys EBOV and likely all other filoviruses at low PVP-I concentrations. Also, as taught in Australian Patent 2014206143 to Molloy et al previously referenced herein, it is known that PVP-I is toxic to immune cells such as monocytes at low PVP-I concentrations. This knowledge combined with the disclosure above of the mechanism of ingress and infection by EBOV has led the current inventors to a new discovery and that is that the repeated intranasal application of PVP-I according to the inventive method would not only eliminate any EBOV present in the nasal passages before an infection can be initiated but would destroy any infected monocytes or neutrophils and eliminate non-infected monocytes or neutrophils present so that could not become subsequently infected by EBOV. In essence, PVP-I application to the nasal passages would transform the nasal passages from a convenient portal of access for EBOV to a secondary barrier of protection from EBOV infection, greatly reducing the overall risk of EBOV infection.

Australian Patent 2014206143 to Molloy et al previously referenced herein teaches that for use in the nasal passages, a suitable concentration of PVP-I is between 0.10% w/v and 2.5% w/v, with the lower value representing the level below which there is little or no effective antimicrobial capacity and the upper value representing the level above which PVP-I is known to cause ciliotoxicity in the nose. For use in the treatment of the common cold the patent teaches against the use of liposomal preparations of PVP-I, as defined in the patent, because of their slower performance and reduced antiviral activity in the face of mucin inactivation, secretory clearance and a most resilient virus, human rhinovirus. In the case of Ebolaviruses, however, which are enveloped viruses and far more sensitive to PVP-I, and with the absence of the rhinorrhoea present in colds, these factors are less applicable. Indeed the slower release and longer residence time associated with liposomal PVP-I formulations, or other slow release/longer residence time forms, for example gels may be an advantage for preventative applications such as EBOV infection. Therefore, the current invention does not exclude liposomal formulations of PVP-I.

As to frequency and timing of application, this will depend on the circumstances of the exposure to EBOV or similar viruses. In the case of healthcare workers who are using PPE and associated barrier techniques while they are exposed to infected individuals, it is not practical to apply a preparation to the nose while the PPE are in place and to do so may increase exposure to viruses. The first opportunity to apply a PVP-I intranasal preparation could be before or while applying PPE (i.e., as part of a PPE "suiting up" regime) or could be at the time of removing the PPE after completing work activities, where the purpose of the application of intranasal PVP-I is to eliminate any viruses that might somehow have circumvented the PPE and other barriers, for example due to failure of a respirator or by the worker inadvertently touching the exterior of a face mask or gown during removal and subsequently touching their nose or eyes allowing the virus to potentially find its way to the nasal passages. In those circumstances, the worker should use the product immediately after removing the PPE in accordance with recommended safe work practices and thereafter at a frequency of up to 12 times daily for the period equivalent to the incubation period for the virus, which in the case of EBOV is up to 21 days after the most recent exposure to the virus.

In the case of people who do not have PPE and may be exposed to virus, such as family members, the PVP-I intranasal preparation would need to be used continuously during the exposure period at a frequency of up to 12 times daily and after the exposure at a similar frequency for the period equivalent to the incubation period for the virus, which in the case of EBOV is up to 21 days after the most recent exposure to the virus.

In every case, the volume of the PVP-I intranasal preparation should be sufficient to reach all parts of the nasal passages, which in the case of a liquid PVP-I intranasal preparation as taught in Australian Patent 2014206143 to Molloy et al previously referenced herein may represent a volume of up to 1 mL applied to each nostril of the exposed person.

The PVP-I intranasal preparation may be in the form a solution, drops, spray, gel, cream, aerosol, or inhalant.

AIV

In the case of AIV and as disclosed by Shinya et al ("Influenza virus receptors in the human airway." Nature, 440: 435-6) H5N1 only productively replicates in the cells of the lower respiratory tract, not the nasal passages. Therefore, the application of PVP-I to the nasal passages would not be regarded by one skilled in the art as a productive means of treating or preventing AIV infection.

However, the present inventors have discovered that where human-human transmission occurs, it would normally occur as the result of the sneezing or coughing of an infected person, with the virus carried by droplets. Such droplets are large enough to deposit in the nasal passages and while the virus may not replicate in the nasal cells, the nasal passages are expected to act as an important initial staging point for establishing infection and/or prior to further ingress to the lower respiratory tract. For example, the virus could be carried by mucociliary clearance to the throat from where it can readily migrate to the bronchi.

Further, in the case of animal-human transmission of AIV, as might occur with people tending, handling or otherwise exposed to animals, especially poultry, infected with AIV, the virus would be carried on dust and other particles and also very likely find its way to the nasal passages and lodge there prior to further migration into the lungs.

In either animal-human or human-human transmission, the virus could also be carried on hands and the person may self-inoculate by touching their eyes or nose with contaminated fingers. Again, the nasal passages could be important in ferrying the virus ultimately to the lungs.

Therefore, the present invention discloses for the first time that whether a person is exposed to infected animals or humans, the application of PVP-I to the nasal passages provides an important protective effect against infection and/or replication/shedding of virus immediately post infection.

It is known that PVP-I rapidly destroys H5N1 and all other influenza viruses, pandemic or otherwise, at low PVP-I concentrations. This knowledge combined with the disclosure above of the mechanism of ingress and infection by AIV has led the current inventors to a new discovery and that is that the repeated intranasal application of PVP-I according to the inventive method would eliminate any AIV present in the nasal passages before the virus can migrate to the lower respiratory tract and establish a productive infection. In essence, the nasal application of PVP-I would transform the nasal passages from a convenient portal of access for AIV to a secondary barrier of protection from AIV infection, greatly reducing the overall risk of AIV infection.

For reasons already discussed, a suitable concentration of PVP-I is between 0.10% w/v and 1.25% w/v, such as about 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1%, 1.05%, 1.1%, 1.15%, or about 1.2% or any range within such concentrations.

As to frequency and timing of application, similar considerations apply to those already discussed for EBOV. In the case of animal or healthcare workers who are using PPE and associated barrier techniques while they are exposed to AIV infected animals or people, the worker should use the product before or while applying PPE or immediately after removing the PPE and thereafter at a frequency of up to 12 times daily for the period equivalent to the incubation period for the virus, which in the case of AIV may be as long as 17 days.

In the case of people who do not have PPE and may be exposed to virus, such as family members, the PVP-I intranasal preparation would need to be used continuously during the exposure period at a frequency of up to 12 times daily and after the exposure at a similar frequency for the period equivalent to the incubation period for the virus, which in the case of AIV is up to 17 days after the most recent exposure to the virus.

In every case, the volume of the PVP-I intranasal preparation should be sufficient to reach all parts of the nasal passages, which in the case of a liquid PVP-I intranasal preparation may represent a volume of up to 1 mL applied to each nostril of the exposed person.

The PVP-I intranasal preparation may be in the form a solution, drops, spray, gel, cream, aerosol, or inhalant.

HP Coronaviruses (e.g., SARS and MERS)

The MERS-CoV causes a LRI, which can result in severe pneumonia with acute respiratory distress and multiple-organ failure leading to a high mortality rate. Like AIV, transmission is likely through airborne droplets or direct or indirect contact with the virus.

Adney et al ("Replication and Shedding of MERS-CoV in Upper Respiratory Tract of Inoculated Dromedary Camels." Emerging Infectious Diseases, 20, 12 (2014): 1999-2005) showed that MERS-CoV actively replicated in the upper respiratory tract of camels.

Memish et al ("Middle East respiratory syndrome coronavirus infections in health care workers." N Engl J Med 369 (2013):884-886) reported asymptomatic carriers of MERS CoV often had mild URI symptoms as well suggesting that the virus might infect the nasal passages of humans, but in a subsequent study Memish et al ("Prevalence of MERS-CoV Nasal Carriage and Compliance With the Saudi Health Recommendations Among Pilgrims Attending the 2013 Hajj." JID 210 (2014): 1067-1072) found no evidence of nasal carriage of MERS-CoV, at least in asymptomatic subjects.

For these reasons and the fact that SARS and MERS are considered lower respiratory tract infections, the application of PVP-I to the nasal passages would not be regarded by one skilled in the art as a productive means of treating or preventing SARS or MERS infections.

However, where human-human transmission occurs, it would normally occur as the result of the sneezing or coughing of an infected person, with the virus carried by droplets. Such droplets are large enough to deposit in the nasal passages and while the virus may not replicate in the nasal cells, the nasal passages may act as an important initial staging point for further ingress to the lower respiratory tract. For example, the virus could be carried by mucociliary clearance to the throat from where it can readily migrate to the bronchi.

Further, in the case of animal-human transmission of SARS or MERS, as might occur with people tending, handling or otherwise exposed to infected animals, the virus would be carried on dust and other particles and also likely find its way to the nasal passages and lodge there prior to further migration into the lungs.

In either animal-human or human-human transmission, the virus could also be carried on hands and the person may self-inoculate by touching their eyes or nose with contaminated fingers. Again, the nasal passages could be important in ferrying the virus ultimately to the lungs. Furthermore, Sungnak and colleagues have recently reported evidence that cells of the nasal passages may be particularly susceptible to infection and have postulated a potential role in initial viral infection, spread and clearance of SARS-CoV-2 (Sungnak, et al., 2020. Nature Comms. 26: 681-687. "SARS-CoV-2 entry factors are highly expressed in nasal epithelial cells together with innate immune genes").

Therefore, the present invention discloses for the first time that whether a person is exposed to infected animals or humans, the application of PVP-I to the nasal passages may provide an important protective effect against ingress to the lower respiratory tract and productive infection. This would be especially important for health care workers and other susceptible people who could be exposed to infected individuals which have tested positive, for instance, for SARS-CoV-2, display the symptoms of COVID-19 disease, or for people who are testing individuals to determine if they are positive for the virus The examples provided herein show that PVP-I also inactivates SARS-CoV-2 (FIGS. 1 and 2).

This knowledge combined with the disclosure above of the mechanism of ingress and infection by SARS or MERS coronaviruses has led the current inventors to a new discovery and that is that the repeated intranasal application of PVP-I according to the inventive method would eliminate any SARS-CoV or MERS-CoV present in the nasal passages before the virus can migrate to the lower respiratory tract and establish a productive infection.

This would include "suppressing' viral infection in an individual infected, for instance with SAR-CoV-2 or other viruses, in order to reduce the risk of transmission.

The concept of "suppressing" viral infection indicates any aspect of viral infection, such as viral replication, time course of infection, amount (titer) of virus, lesions, and/or one or more symptoms is curtailed, inhibited, or reduced (in terms of severity and/or duration) in an individual or population of individuals treated with a PVP-I composition in accordance with the invention as compared to an aspect of viral infection in an individual or population of individuals not treated in accordance with the invention. Reduction in viral titer includes, but is not limited to, elimination of the virus from an infected site or individual. Viral infection can be assessed by any means known in the art, including, but not limited to, measurement of virus particles, viral nucleic acid or viral antigens, detection of symptoms and detection and/or measurement of anti-virus antibodies. Anti-virus antibodies are widely used to detect and monitor viral infection and generally are commercially available. In addition, viral infection can be assessed by other means known in the art including, but not limited to, PCR, in situ hybridization with virus specific probes, $TCID_{50}$ assays, infectious center assays, plaque assays, etc.

For reasons already discussed, a suitable concentration of PVP-I is between 0.10% w/v and 1.25% w/v, such as about 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1%, 1.05%, 1.1%, 1.15%, or about 1.2% or any range within such concentrations.

As to frequency and timing of application, similar considerations apply to those already discussed for EBOV and AIV. In the case of animal or healthcare workers who are using PPE and associated barrier techniques while they are exposed to AIV infected animals or people, the worker should use the product prior to or at the same time as applying PPE, or immediately after removing the PPE and thereafter at a frequency of up to 12 times daily for the period equivalent to the incubation period for the virus, which in the case of SARS is up to 10 days and for MERS is up to 14 days.

In the case of people who do not have PPE and may be exposed to virus, such as family members, the PVP-I intranasal preparation would need to be used continuously during the exposure period at a frequency of up to 12 times daily and after the exposure at a similar frequency for the period equivalent to the incubation period for the virus, or up to 10 days for SARS and 14 days for MERS after the most recent exposure to the virus.

In every case, the volume of the PVP-I intranasal preparation should be sufficient to reach all parts of the nasal passages, which in the case of a liquid PVP-I intranasal preparation may represent a volume of up to 1 mL applied to each nostril of the exposed person.

The PVP-I intranasal preparation may be in the form a solution, drops, spray, gel, cream, aerosol, or inhalant.

In relation to the HP viruses discussed above in certain embodiments the nasal application provides a clinically significant Log reduction of at least several log units (e.g. 2-4 log units) within about 5-20 mins which persists for about 8 hrs after being exposed to said virus after one application within the nasal passage. In an embodiment the composition provides a clinically significant Log reduction of at least several log units (e.g. 2-4 log units) within about 5-20 mins which persists for about 6 hrs after being exposed to said virus after one application within the nasal passage. In an embodiment the composition provides a clinically significant Log reduction of at least several log units (e.g. 2-4 log units) within about 5-20 mins which persists for about 4 hrs after being exposed to said virus after one application within the nasal passage. In another embodiment the composition provides a clinically significant Log reduction of at least several log units (e.g. 2-4 log units) within about 5-20 mins which persists for 2 hrs after being exposed to said virus after one application within the nasal passage. In another embodiment the composition provides a clinically significant Log reduction of at least several log units (e.g. 2-4 log units) within about 5-20 mins which persists for 1 hr after being exposed to said virus after one application within the nasal passage.

In relation to the HP viruses discussed above in certain embodiments the nasal application provides a clinically significant Log reduction of at least several log units (e.g. 2-4 log units) within about 10 mins which persists for about 8 hrs after being exposed to said virus after one application within the nasal passage. In an embodiment the composition provides a clinically significant Log reduction of at least several log units (e.g. 2-4 log units) within about 10 mins which persists for about 6 hrs after being exposed to said virus after one application within the nasal passage. In an embodiment the composition provides a clinically significant Log reduction of at least several log units (e.g. 2-4 log units) within about 10 mins which persists for about 4 hrs after being exposed to said virus after one application within the nasal passage. In another embodiment the composition provides a clinically significant Log reduction of at least several log units (e.g. 2-4 log units) within about 10 mins which persists for 2 hrs after being exposed to said virus after one application within the nasal passage. In another embodiment the composition provides a clinically significant Log reduction of at least several log units (e.g. 2-4 log units) within about 10 mins which persists for 1 hr after being exposed to said virus after one application within the nasal passage.

Secondary Infections

It is well known that so called "secondary infections" can be a common complication of a primary viral infection, particularly in the case of a primary respiratory viral disease. These secondary infections are often bacterial infections. Secondary infections occurs during or after an infection from another pathogen, commonly viruses. These secondary diseases are thought to be facilitated by a number of factors, including viral mediated enhanced attachment and colonization, viral mediated enhanced pathogenesis and viral mediated immune-modulation. Secondary infections are responsible for increased morbidity and in some cases mortality and have been shown to increase the societal and individual impact of HP viruses. For example, during the H1N1 2009 influenza pandemic secondary infection by a variety of micro-organisms including *Mycoplasma pneumoniae, S. aureus, K. pneumoniae, S. pneumoniae, M catarrhalis, P. aeruginosa, S. pyogenes*, and *Streptococcus agalactiae* was shown to be present in approximately a third to a half of all fatalities (Morris et al., *Front. Microbiol.* 2017; 8: 1041 "Secondary Bacterial Infections Associated with Influenza Pandemics" and references therein). Similarly secondary infections have been commonly reported following autopsy of fatal COVID-19 disease there are concerns that these may contribute to mortality and morbidity associated with the recent pandemic (Cox et al., *Lancet, Microbe* 2020; 1: E11 "Co-infections: potentially lethal and unexplored in COVID-19", and references therein). These secondary infections present a complex diagnostic challenge since they may comprise a variety of species and may prove difficult to resolve from micro-organisms colonizing the patient benignly or in some cases previously benign organisms may become pathogenic following the primary infection. PVP-I is reported to have broad spectrum anti-microbial activity and rapidly inactivates a wide range of micro-organisms including antibiotic resistant strains (Kanagalingam, et al., *Int J Clin Practice.* 2015 69; 11: 1247-1256, "Practical use of povidone-iodine antiseptic in the maintenance of oral health and in the prevention and treatment of common oropharyngeal infections" and references therein). The use of PVP-I has been proposed as a universal "disinfectant" for the purposes maintaining, for example, oral health associated with microbial infections. Importantly, due to its mode of action and broad spectrum activity it is not expected that knowledge of the identity or antibiotic susceptibility of the micro-organism responsible for the secondary infection will be required nor the lack of this knowledge limit the utility of PVP-I.

Secondary infections, often associated with bacteria and fungi, are a known cause of serious morbidity and mortality in viral diseases, particularly respiratory viruses. Secondary infections are also thought to have played a role in recent pandemics caused by HP viruses. They are often difficult to diagnose and, for example in the case of antibiotic resistant organisms, can pose treatment challenges. The primary virus infection is thought to predispose a patient to secondary diseases through, for example, promoting colonization, immune-modulation and other factors such as facilitating increased virulence. Diseases such as bacterial pneumonia caused by secondary infections are a result of bacterial infection of the lower respiratory tract.

For these reasons the application of PVP-I to the nasal passages would not be regarded by one skilled in the art as a productive means of treating or preventing secondary infections.

Therefore, the present invention discloses for the first time that whether a person is exposed to infection with a HP virus, the application of PVP-I to the nasal passages may provide an important protective effect against secondary infections and the diseases associated with secondary infections. This would be especially important for health care workers and other susceptible people who may be at increased risk.

It is known that PVP-I has a broad spectrum antimicrobial effect (2006), (previously referenced herein), and is unaffected by antibiotic resistance. In some cases, the organisms involved in secondary diseases may colonise the nasal passages in a benign fashion prior to the primary infection.

This knowledge combined with the disclosure above of the mechanism of ingress and infection by HP viruses has led the current inventors to a new discovery and that is that the repeated intranasal application of PVP-I according to the inventive method would eliminate micro-organisms present in the nasal passages, thereby preventing the promotion of colonization and exacerbated disease, and limit their spread before they can migrate to the lower respiratory tract (or elsewhere) and establish a productive secondary infection.

For reasons already discussed, a suitable concentration of PVP-I is between 0.10% w/v and 1.25% w/v, such as about 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1%, 1.05%, 1.1%, 1.15%, or about 1.2% or any range within such concentrations.

As to frequency and timing of application, similar considerations apply to those already discussed for primary infection with HP viruses. In the case of animal or healthcare workers who are using PPE and associated barrier techniques while they are exposed to HP virus infected animals or people, the worker should use the product prior to or at the same time as applying PPE, or immediately after removing the PPE and thereafter at a frequency of up to 12 times daily for the period equivalent to the incubation period for the virus.

In the case of people who do not have PPE and may be exposed to virus, such as family members, the PVP-I intranasal preparation would need to be used continuously during the exposure period at a frequency of up to 12 times daily and after the exposure at a similar frequency for the period equivalent to the incubation period for the virus.

In every case, the volume of the PVP-I intranasal preparation should be sufficient to reach all parts of the nasal passages, which in the case of a liquid PVP-I intranasal preparation may represent a volume of up to 1 mL applied to each nostril of the exposed person.

It is intended that the preparations be applied at "ambient temperature" which refers to the temperature in the environment at which the method of the current invention is conducted. Typically ambient temperature will be about 10° C. to about 30° C. Importantly the term "ambient temperature" means that neither the formulation nor the nasal passages of the subject to be treated are exposed to external heating in carrying out the method of the present invention.

Intranasal Preparations:

As disclosed herein the PVP-I intranasal preparations may be in the form a solution, drops, spray, gel, cream, aerosol, or inhalant.

Suitable concentration of PVP-I is between 0.10% w/v and 1.25% w/v, such as about 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95%, 1%, 1.05%, 1.1%, 1.15%, or about 1.2% or any range within such concentrations.

In certain embodiments the PVP-I intranasal preparations are aqueous based intranasal preparations where water makes up from about 80% w/v to about 96% w/v of the total preparation.

In certain embodiments the PVP-I preparations disclosed herein additionally includes an amount of iodide and/or iodate salts of from about 0.003 to about 0.05% w/v of the total preparation.

In certain embodiments the PVP-I preparations disclosed herein may also include one or more of the following: solubilising agents, polar solvents, dry acidulant, sequestrants, alkaline agents, counter-irritant agents, local anaesthetic and preservatives.

In certain embodiments the PVP-I intranasal preparations are aqueous based intranasal preparations where water makes up from about 80% w/v to about 96% w/v of the total preparation and has a pH of from about 2-7 such as a pH range of about 3-6.

In certain embodiments the PVP-I preparations disclosed herein additionally includes an amount of humectant such as hyaluronic acid, polyethylene glycol or glycerol (glycerine) from about 1 to about 10% w/v of the total preparation.

In certain embodiments the PVP-I preparations disclosed herein additionally includes an amount of a polar solvent, such as ethanol, from about 0.2 to about 2% w/v of the total preparation.

In certain embodiments the PVP-I preparations disclosed herein additionally includes an amount of a counter-irritant or local anaesthetic, such as menthol, from about 0.001 to about 1% w/v of the total preparation.

In certain embodiments the PVP-I preparations disclosed herein additionally includes an amount of a preservative, such as a quaternary ammonium salt preservative, from about 0.01 to about 0.5% w/v of the total preparation.

In certain embodiments the PVP-I preparations disclosed herein additionally includes an amount of buffer such as sodium phosphate, citrate or acetate from about 0.05 to about 0.5% w/v of the total preparation.

The pharmaceutical preparation may further comprise at least one pharmaceutically acceptable diluent, excipient or carrier.

The diluent, excipient or carrier may be a flavor agent, sweetener, colouring agent, solvent, buffer, alcohol, polymer, surfactant or other diluent, excipient or carrier designed to optimize the nasal delivery, intranasal distribution, stability, effectiveness, acceptability, tolerability of the preparation.

EXAMPLES

Aqueous-Intranasal Preparation Examples:

Example 1

| Per 100 mL | g | % w/v |
|---|---|---|
| PVP-I | 0.50 | 0.50% |
| Potassium Iodide | 0.010 | 0.010% |
| Hyaluronic Acid | 1.00 | 1.00% |
| Sodium Citrate | 0.15 | 0.15% |
| Eucalyptus | 0.01 | 0.010% |
| Ethanol | 0.49 | 0.490% |
| Benzalkonium Chloride | 0.01 | 0.01% |
| Water | 97.83 | 97.83% |
| | 100.00 | 100.0% |

Example 2

| Per 100 mL | g | % w/v |
|---|---|---|
| PVP-I | 0.50 | 0.50% |
| Potassium Iodide | 0.010 | 0.010% |
| Potassium Iodate | 0.005 | 0.005% |
| Glycerol | 5.00 | 5.00% |
| Sodium Hydrogen Phosphate | 0.15 | 0.15% |
| Ethanol | 0.49 | 0.49% |
| Menthol | 0.01 | 0.010% |
| Water | 93.84 | 93.84% |
| | 100.00 | 100.0% |

Example 3

| Per 100 mL | g | % w/v |
|---|---|---|
| PVP-I | 0.50 | 0.50% |
| Potassium Iodide | 0.010 | 0.010% |
| Potassium Iodate | 0.005 | 0.005% |
| Glycerol | 5.00 | 5.00% |
| Sodium Hydrogen Phosphate | 0.15 | 0.15% |
| Sodium Hydroxide | 0.75 | 0.75% |
| Ethanol | 0.49 | 0.49% |
| Menthol | 0.01 | 0.010% |
| Water | 93.08 | 93.08% |
| | 100.00 | 100.0% |

Example 4

| Per 100 mL | g | % w/v |
|---|---|---|
| PVP-I | 0.50 | 0.50% |
| Povidone | 0.300 | 0.30% |
| Glycerol | 3.00 | 3.00% |
| Sodium Citrate | 0.15 | 0.15% |
| Citral | 0.49 | 0.49% |
| Water | 95.56 | 95.56% |
| | 100.00 | 100.0% |

Example 5

| Per 100 mL | g |
|---|---|
| PVP-I | 0.50 |
| Povidone | 0.030 |
| Potassium Iodide | 0.010 |
| Polyethylene Glycol 4000 | 2.00 |
| Tween 20 | 0.05 |
| Sodium Hydrogen Phosphate | 0.15 |
| Ethanol | 0.49 |
| Peppermint Oil | 0.01 |
| Water | 96.76 |
| | 100.00 |

Example 6

| Per 100 mL | g | % w/v |
|---|---|---|
| PVP-I | 0.50 | 0.50% |
| Sodium Iodide | 0.010 | 0.010% |
| Sodium Acetate | 0.15 | 0.15% |
| Sorbitol | 0.01 | 0.010% |
| Lutrol | 0.50 | 0.500% |
| Water | 98.83 | 98.83% |
| | 100.00 | 100.0% |

Example 7

| Per 100 mL | g | % w/v |
|---|---|---|
| PVP-I | 0.50 | 0.50% |
| Lutrol | 2.00 | 2.00% |
| Sodium Citrate | 0.15 | 0.15% |
| Saccharine | 0.01 | 0.010% |
| Water | 97.34 | 97.34% |
| | 100.00 | 100.0% |

Example 8

| Per 100 mL | g | % w/v |
|---|---|---|
| PVP-I | 0.50 | 0.50% |
| Polyethylene Glycol 4000 | 3.00 | 3.00% |
| Sodium Hydrogen Phosphate | 0.15 | 0.15% |
| Xylitol | 1.00 | 1.00% |
| Water | 95.35 | 95.35% |
| | 100.00 | 100.0% |

Example 9

| Per 100 mL | g | % w/v |
|---|---|---|
| PVP-I | 0.50 | 0.50% |
| Triacetin | 2.00 | 2.00% |
| Sodium Acetate | 0.15 | 0.15% |

Example 10

| Per 100 mL | g | % w/v |
|---|---|---|
| PVP-I | 1.00 | 1.00% |
| Potassium Iodide | 0.02 | 0.02% |
| Hyaluronic Acid | 0.50 | 0.50% |
| Sodium Citrate | 0.15 | 0.15% |
| Eucalyptus | 0.01 | 0.01% |
| Ethanol | 0.49 | 0.49% |
| Benzalkonium Chloride | 0.01 | 0.01% |
| Water | 97.82 | 97.82% |
|  | 100.00 | 100.00% |

Example 11

| Per 100 mL | g | % w/v |
|---|---|---|
| PVP-I | 1.00 | 1.00% |
| Potassium Iodide | 0.02 | 0.02% |
| Potassium Iodate | 0.01 | 0.01% |
| Glycerol | 5.00 | 5.00% |
| Sodium Hydrogen Phosphate | 0.15 | 0.15% |
| Ethanol | 0.49 | 0.49% |
| Menthol | 0.01 | 0.01% |
| Water | 93.32 | 93.32% |
|  | 100.00 | 100.00% |

Example 12

| Per 100 mL | g | % w/v |
|---|---|---|
| PVP-I | 1.00 | 1.00% |
| Povidone | 0.60 | 0.60% |
| Glycerol | 3.00 | 3.00% |
| Sodium Citrate | 0.15 | 0.15% |
| Citral | 0.49 | 0.49% |
| Water | 94.76 | 94.76% |
|  | 100.00 | 100.00% |

Example 13

| Per 100 mL | g | % w/v |
|---|---|---|
| PVP-I | 1.00 | 1.00% |
| Povidone | 0.06 | 0.06% |
| Potassium Iodide | 0.02 | 0.02% |
| Polyethylene Glycol 4000 | 2.00 | 2.00% |
| Tween 20 | 0.05 | 0.05% |
| Ethanol | 0.49 | 0.49% |
| Eucalyptus Oil | 0.01 | 0.010% |
| Water | 96.80 | 96.80% |
|  | 100.00 | 100.0% |

-continued

| Per 100 mL | g | % w/v |
|---|---|---|
| Tween 20 | 0.05 | 0.05% |
| Sodium Hydrogen Phosphate | 0.15 | 0.15% |
| Ethanol | 0.49 | 0.49% |
| Peppermint Oil | 0.01 | 0.01% |
| Water | 96.22 | 96.22% |
|  | 100.00 | 100.00% |

Example 14

| Per 100 mL | g | % w/v |
|---|---|---|
| PVP-I | 1.00 | 1.00% |
| Sodium Iodide | 0.02 | 0.02% |
| Sodium Acetate | 0.15 | 0.15% |
| Sorbitol | 0.01 | 0.01% |
| Lutrol | 0.50 | 0.50% |
| Water | 98.32 | 98.32% |
|  | 100.00 | 100.00% |

Example 15

| Per 100 mL | g | % w/v |
|---|---|---|
| PVP-I | 1.00 | 0.50% |
| Lutrol | 2.00 | 2.00% |
| Sodium Citrate | 0.15 | 0.15% |
| Saccharine | 0.01 | 0.01% |
| Water | 96.84 | 96.84% |
|  | 100.00 | 100.00% |

Example 16

| Per 100 mL | g | % w/v |
|---|---|---|
| PVP-I | 1.00 | 0.50% |
| Polyethylene Glycol 4000 | 3.00 | 3.00% |
| Sodium Hydrogen Phosphate | 0.15 | 0.15% |
| Xylitol | 1.00 | 1.00% |
| Water | 94.85 | 94.85% |
|  | 100.00 | 100.00% |

Example 17

| Per 100 mL | g | % w/v |
|---|---|---|
| PVP-I | 1.00 | 0.50% |
| Triacetin | 2.00 | 2.00% |
| Sodium Acetate | 0.15 | 0.15% |
| Tween 20 | 0.05 | 0.05% |
| Ethanol | 0.49 | 0.49% |

Example 18

| Per 100 mL | g | % w/v |
|---|---|---|
| PVP-I | 0.20 | 0.20% |
| Potassium Iodide | 0.02 | 0.02% |
| Hyaluronic Acid | 0.50 | 0.50% |
| Sodium Citrate | 0.15 | 0.15% |
| Eucalyptus | 0.01 | 0.01% |
| Ethanol | 0.49 | 0.49% |
| Benzalkonium Chloride | 0.01 | 0.01% |
| Water | 98.62 | 98.62% |
| | 100.00 | 100.00% |

Example 19

| Per 100 mL | g | % w/v |
|---|---|---|
| PVP-I | 0.20 | 0.20% |
| Potassium Iodide | 0.02 | 0.02% |
| Potassium Iodate | 0.01 | 0.01% |
| Glycerol | 5.00 | 5.00% |
| Sodium Hydrogen Phosphate | 0.15 | 0.15% |
| Ethanol | 0.49 | 0.49% |
| Menthol | 0.01 | 0.01% |
| Water | 93.32 | 93.32% |
| | 100.00 | 100.00% |

Example 20

| Per 100 mL | g | % w/v |
|---|---|---|
| PVP-I | 0.20 | 0.20% |
| Povidone | 0.60 | 0.60% |
| Glycerol | 3.00 | 3.00% |
| Sodium Citrate | 0.15 | 0.15% |
| Citral | 0.49 | 0.49% |
| Water | 95.56 | 95.56% |
| | 100.00 | 100.00% |

Example 21

| Per 100 mL | g | % w/v |
|---|---|---|
| PVP-I | 0.20 | 1.00% |
| Povidone | 0.06 | 0.06% |
| Potassium Iodide | 0.02 | 0.02% |
| Polyethylene Glycol 4000 | 2.00 | 2.00% |
| Tween 20 | 0.05 | 0.05% |
| Sodium Hydrogen Phosphate | 0.15 | 0.15% |
| Eucalyptus Oil | 0.01 | 0.01% |
| Water | 96.30 | 96.30% |
| | 100.00 | 100.00% |

Example 22

| Per 100 mL | g | % w/v |
|---|---|---|
| Ethanol | 0.49 | 0.49% |
| Peppermint Oil | 0.01 | 0.01% |
| Water | 97.02 | 97.02% |
| | 100.00 | 100.0% |

| Per 100 mL | g | % w/v |
|---|---|---|
| PVP-I | 0.20 | 1.00% |
| Sodium Iodide | 0.02 | 0.02% |
| Sodium Acetate | 0.15 | 0.15% |
| Sorbitol | 0.01 | 0.01% |
| Tween 20 | | |
| Lutrol | 0.50 | 0.50% |
| Water | 99.12 | 99.12% |
| | 100.00 | 100.0% |

Example 23

| Per 100 mL | g | % w/v |
|---|---|---|
| PVP-I | 0.20 | 0.50% |
| Lutrol | 2.00 | 2.00% |
| Sodium Citrate | 0.15 | 0.15% |
| Saccharine | 0.01 | 0.01% |
| Water | 97.64 | 97.64% |
| | 100.00 | 100.00% |

Example 24

| Per 100 mL | g | % w/v |
|---|---|---|
| PVP-I | 0.20 | 0.50% |
| Polyethylene Glycol 4000 | 3.00 | 3.00% |
| Sodium Hydrogen Phosphate | 0.15 | 0.15% |
| Xylitol | 1.00 | 1.00% |
| Water | 95.65 | 95.65% |
| | 100.00 | 100.00% |

Example 25

| Per 100 mL | g | % w/v |
|---|---|---|
| PVP-I | 0.20 | 0.50% |
| Triacetin | 2.00 | 2.00% |
| Sodium Acetate | 0.15 | 0.15% |
| Tween 20 | 0.05 | 0.05% |
| Ethanol | 0.49 | 0.49% |
| Eucalyptus Oil | 0.01 | 0.01% |
| Water | 96.30 | 96.30% |
| | 100.00 | 100.00% |

Biological Data:

a) SARS-CoV-2

PVP-I nasal intranasal preparation of the examples inactivates SARS-CoV-2 in a cell culture system Introduction This study assessed the ability of PVP-I to inactivate SARS-CoV-2, shown to replicate efficiently within the upper respiratory tract. PVP-I was assessed against saline and media only controls in parallel to assess the presence/absence of virucidal activity.

Study Objective:

The objective of this study is to compare and assess the virucidal activity of PVP-I against the SARS-CoV-2 strain (BetaCoV/Australia/VIC01/2020) in the African Green Monkey Kidney (Vero) human cell line.

The impact on virus replication will be qualitatively assessed for SARS-CoV-2 RNA using a SARS specific TaqMan Real-time PCR assay targeting the E-gene.

Materials:

Virus

SARS-CoV-2 (BetaCoV/Australia/VIC01/2020) was isolated and grown by the Victorian Infectious Diseases Reference Laboratory from a positive patient specimen in January, 2020. Whole-genome sequencing confirmed the presence of SARS-CoV-2 (GenBank ID: MT007544).

Placebo and Povidone Iodine Solutions

PVP-I examples according to the description were prepared at a concentration of PVP-I between 0.1% w/v and 1.25% w/v (designated as "PVP-I"—this examples section)

Cells

Vero cells were grown in Eagle's Minimum Essential Medium (Sigma-Aldrich, North Ryde, Australia) catalogue number (M2279), supplemented with 1× Non-essential amino acids (NEAA) (Gibco, Mount Waverley, Australia; catalogue number 11140050) and 10% heat-inactivated foetal bovine serum (FBS: Bovogen, Melbourne, Australia; catalogue number SFBS, lot #1502B).

Methods:

Plating 96-Well Plates

Vero cells were trypsinised, counted and seeded into 96-well plates at a cell density of 1×104 cells/well in 200 ul media and incubated at 37° C., 5% $CO_2$. Outer perimeter wells of the plate were not used, to minimise potential edge effects.

Incubation of Virus with Treatment Solutions 95 ul of each test solution (saline or PVP-I) was incubated with 5 ul of each virus at 37° C. for 1 minute. At the end of incubation, the test solution/virus mix was diluted 1:10 with ice cold EMEM 2% FBS media. Immediately after adding ice cold media, 100 ul of test mixture for the samples was added to the plates in triplicate (column 2 below). Note: PVP-I was tested in duplicate (PVP-I #1, PVP-I #2). Samples were thoroughly mixed and 100 ul transferred to column 3 with fresh pipette tips. 100 ul was transferred from column 3 to column 4 and so on until column 10. 100 ul from column 10 was discarded, leaving a final volume of 200 ul in the wells. Column 11 contained cells alone with fresh EMEM 2% which served as a no virus control. Plates were incubated at 37° C., 5% $CO_2$ atmosphere for 48 hours before harvesting.

| | | dilution factor: | | | | | | | | | |
|---|---|---|---|---|---|---|---|---|---|---|---|
| | | 3 | 9 | 27 | 81 | 243 | 729 | 2187 | 6561 | 19683 | |
| | | | | | | log(10) dilution | | | | | |
| | | 0.5 | 1 | 1.4 | 1.9 | 2.4 | 2.9 | 3.3 | 3.8 | 4.3 | Uninfected |
| | | 2 | 3 | 4 | 5 | 6 | 7 | 8 | 9 | 10 | CONTROL |
| Sample 1 | A | | | | | | | | | | |
| | B | | | | | | | | | | |
| | C | | | | | | | | | | |
| | D | | | | | | | | | | |
| Sample 2 | E | | | | | | | | | | |
| | F | | | | | | | | | | |
| | G | | | | | | | | | | |
| | H | | | | | | | | | | |

Purification of SARS-CoV RNA.

SARS-CoV-2 RNA was purified from 200 ul supernatant/media from each well of the 96-well plates using the QIAamp 96 virus QIAcube HT Kit and processed on the QIAcube robotic extraction platform (QIAgen, Hilden, Germany) to confirm the presence/absence of replicating virus.

Taqman RT-PCR of SARS-CoV RNA.

Purified SARS-CoV-2 RNA was reverse transcribed to cDNA using the Bioline Sensifast cDNA kit (Catalogue number CSA-01148; London, UK). Real-time assays were performed using the published SARS E-gene assay[1] with primers and probes (IDT, Singapore) and ABI TaqMan Fast Universal PCR Master Mix (2×) (catalogue number 4352042; Thermofisher, Vilnius, Lithuania). Assays were performed on a Thermofisher ABI 7500 Fast Real Time PCR machine.

Results:

Taqman RT-PCR Assessment of SARS-CoV-2 RNA in 96-Well Plate Supernatants.

To confirm that the presence or absence of replicating SARS-CoV-2, 200 ul supernatant samples from all triplicate wells were analysed for the presence of SARS-CoV-2 RNA by Taqman RT-PCR.

To establish a baseline of RT-PCR cycle threshold (Ct) values for non-replicating, non-viable virus, initial inoculum samples (0 h post infection) were titrated 1:3 (~0.5 log 10) to 1:19683 (4.3 log 10) and subjected to the E-gene specific Taqman RT-PCR. SARS-CoV-2 alone, in the presence of saline, and Nasodine, show a linear relationship between Ct-value and dilution factor (see FIGS. 1A, 2A). Overlapping values were observed for all conditions, indicating that the test solutions did not have any effect in the ability of our assay to detect nucleic acid by real-time RT-PCR.

48 hr Study

Following 48 h of incubation on Vero cells, SARS-CoV-2 displayed robust replication both within and without the presence of saline (FIG. 1B). When incubated in the presence of PVP-I, an almost linear relationship was observed between viral RNA Ct-values and dilution factor (where Ct-values increased as the dilution factor increased), at similar levels to inoculum only controls, indicating the absence of any measurable viral growth after PVP-I treatment and a reduction in detectable by at least −2.4 Log 10 in the PVP-I samples, representing a reduction in viral RNA copies of over 99%.

Conclusion of 48 h Study:

The objective of this study was to compare and assess the virucidal activity of PVP-I solution against the newly emerged SARS-CoV-2, the causative agent of COVID-19 disease. Using real-time TaqMan RT-PCR methods it was determined that PVP-I possesses clear virucidal activity against SARS-CoV-2 (−2.4 Log 10 reduction, or >99% kill) compared to saline alone.

96 hr Study

Following 96 h of incubation on Vero cells, SARS-CoV-2 in media alone displayed robust replication (FIG. 2B), as shown by a decrease in Ct-value. When incubated in the presence of Nasodine, an almost linear relationship was observed between viral RNA Ct-values and dilution factor (where Ct-values increased as the dilution factor increased), at similar levels to inoculum only controls, indicating the absence of any measurable viral growth after Nasodine treatment and a reduction in detectable virus by at least −3.6 Log 10 in the Nasodine samples, representing a reduction in viral RNA copies of over 99.97%.

CONCLUSION

The objective of this study was to compare and assess the virucidal activity of PVP-I solution against the newly emerged SARS-CoV-2, the causative agent of COVID-19 disease. Using real-time TaqMan RT-PCR methods it was determined that PVP-I possesses clear virucidal activity against SARS-CoV-2 and based on the RT-PCR data obtained effectively eliminated the replication competent SARS-CoV-2 present in the sample compared to media alone as evidenced by the lack of viral replication in the dilutions cultured from PVP-I treated samples compared to the equivalent untreated samples. A comparison of the viral RNA copy number associated with cultures derived from the least diluted untreated control sample with the equivalent PVP-I sample indicated a −3.6 Log 10 reduction in RNA copies or a >99.97% PVP-I mediated kill. The extent of this quantifiable "kill" is limited by the titre of measurable viable virus in the control sample.

The invention claimed is:

1. A method of decreasing the release of infective SARS-CoV-2 from the nose of a person infected with SARS-CoV-2, the method comprising application to the nasal passages of the infected person an effective amount of a pharmaceutical preparation comprising povidone-iodine (PVP-I) at a concentration of greater than 0.10% w/v and less than about 1.25% w/v.

2. The method as claimed in claim 1, wherein the PVP-I concentration in the pharmaceutical preparation applied to the nasal passages is about 0.1% to about 1.0% w/v.

3. The method as claimed in claim 2, wherein the PVP-I concentration in the pharmaceutical preparation applied to the nasal passages is about 0.2% to about 0.5% w/v.

4. The method as claimed in claim 1, wherein the pharmaceutical preparation is applied at a frequency of between 1 and 12 times daily commencing before, after or around the time of exposure to the SARS-CoV-2 and/or thereafter.

* * * * *